United States Patent
Rudin et al.

(10) Patent No.: US 6,285,739 B1
(45) Date of Patent: Sep. 4, 2001

(54) RADIOGRAPHIC IMAGING APPARATUS AND METHOD FOR VASCULAR INTERVENTIONS

(75) Inventors: Stephen Rudin, Williamsville; Daniel R. Bednarek, Cheektowaga; Baruch B. Lieber, East Amherst, all of NY (US); Ajay Kumar Wakhloo, Key Biscayne, FL (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/507,518

(22) Filed: Feb. 18, 2000

Related U.S. Application Data
(60) Provisional application No. 60/120,675, filed on Feb. 19, 1999.

(51) Int. Cl.[7] .................................................. H05G 1/64
(52) U.S. Cl. ............................ 378/98.8; 378/62; 378/98; 378/98.2
(58) Field of Search ......................... 378/62, 98, 98.2, 378/98.8

(56) References Cited

U.S. PATENT DOCUMENTS

| | | | |
|---|---|---|---|
| 4,142,101 | 2/1979 | Yin .................................... 250/363 |
| 4,492,119 | * 1/1985 | Dulapa et al. ......................... 73/621 |
| 5,117,446 | * 5/1992 | Haaker et al. ....................... 378/98.3 |
| 5,282,236 | * 1/1994 | Hayes et al. .......................... 378/182 |
| 5,355,309 | * 10/1994 | Eberhard et al. ..................... 378/15 |
| 5,391,879 | * 2/1995 | Tran et al. ............................. 250/367 |
| 5,465,284 | * 11/1995 | Karellas ................................. 378/62 |
| 5,574,764 | * 11/1996 | Granfors et al. ..................... 378/98.7 |
| 5,594,253 | * 1/1997 | Bueno et al. ....................... 250/486.1 |
| 5,773,832 | * 6/1998 | Sayed et al. ..................... 250/370.09 |
| 5,818,053 | * 10/1998 | Tran ................................. 250/370.09 |
| 5,820,623 | * 10/1998 | Ng ........................................... 606/1 |
| 5,875,226 | 2/1999 | Yokouchi et al. ................... 378/98.2 |
| 5,912,943 | * 6/1999 | Deucher et al. .................... 378/98.8 |
| 5,917,883 | 6/1999 | Khutoryansky et al. ............ 378/116 |

* cited by examiner

Primary Examiner—Robert H. Kim
Assistant Examiner—Allen C Ho
(74) Attorney, Agent, or Firm—Hodgson Russ LLP

(57) ABSTRACT

A radiographic imaging apparatus and method for vascular interventions for acquiring very high resolution radiographic images over a small region of interest (ROI). The apparatus and associated method employs digital solid state x-ray image detectors for the medical imaging application of angiography. A mechanical arrangement, for example an arm attached to an existing large area x-ray detector, allows the small area ROI digital detector to be temporarily positioned over a region located by the standard large area imager so that additional very high resolution digital images may be obtained over the ROI.

47 Claims, 6 Drawing Sheets

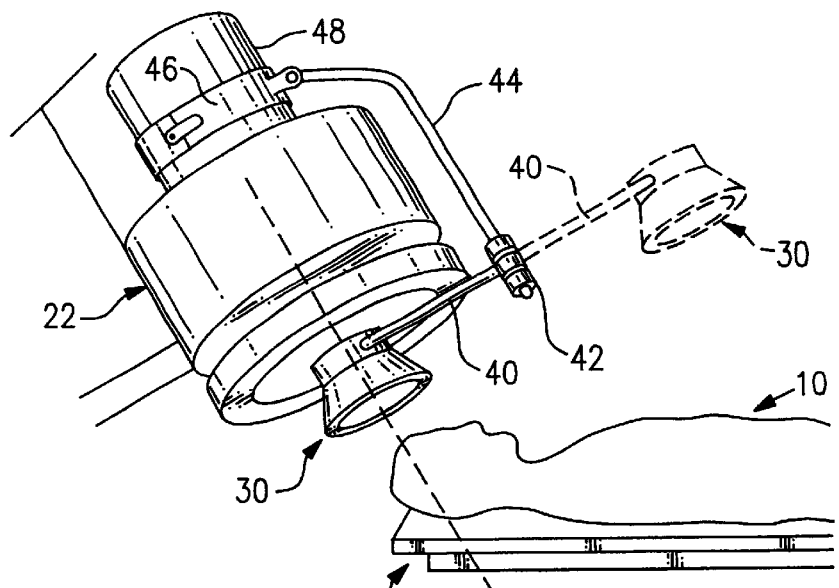
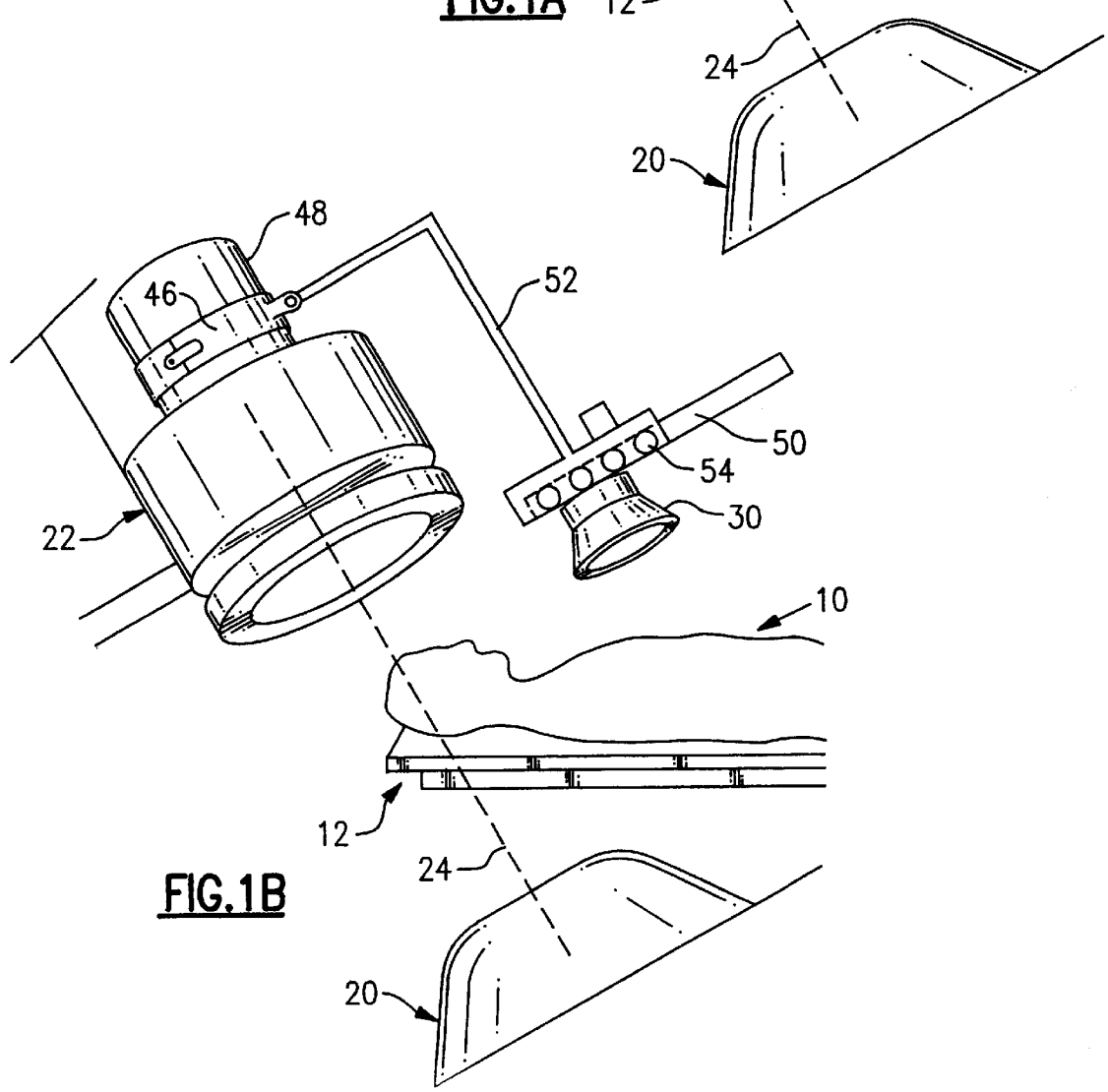
FIG.1A
FIG.1B

RADIOGRAPHIC IMAGING APPARATUS AND METHOD FOR VASCULAR INTERVENTIONS

CROSS-REFERENCE TO RELATED APPLICATION

Applicants hereby claim priority based on Provisional Application No. 60/120,675 filed Feb. 19, 1999, and entitled "Radiographic Imaging Apparatus and Method for Vascular Interventions," which is incorporated herein by reference.

BACKGROUND OF THE INVENTION

This invention relates to the art of radiography, and more particularly to a new and improved radiographic imaging apparatus and method optimized for vascular interventions for providing region of interest micro-angiography.

After heart disease and cancer the most significant cause of death in the United States is cerebrovascular disease. The three most common cerebrovascular pathologies are stenoses or narrowing due to vessel degeneration, aneurysms or bulges, and arteriovenous malformations (AVM) which act as short circuits. Hemorrhage and other incidents due to these pathologies or acute thrombogenesis leading to vessel constriction or blockage can lead to stroke resulting in death or devastating effects to the individual who survives.

Often in the past the treatment of choice, although not always possible, was invasive surgery that can carry substantial risks of its own. Image-guided minimally invasive endovascular treatments primarily radiographically guided are becoming increasingly preferred. As these new procedures evolve with smaller and finer catheters and devices, they are placing greater requirements on image quality. Thus, there is a growing requirement for high spatial resolution during endovascular interventions. Clinical decisions for balloon expansion of a stent or attempts to mold the stent within the treated vessel depend upon images with adequate detail. Seeing the spatial relationship between overlapping stents where these may be required is now difficult. Detecting the drift of stents during the placement process is difficult. With newer stents having smaller gauge wire and more complex design it is becoming very difficult to see even the gross shape of the stent let alone to determine the status of the individual segments or wires. As the endovascular devices progress toward treatments of smaller vessels within or beyond the circle of Willis, there will be the additional concern about disturbing or blocking the origin of perforators. These perforators that are 50–500 $\mu$m in diameter are often extremely important vessels for specific, key neurological functions, and if blocked can produce devastating deficits in the patient. Perforators seen during invasive micro-surgery typically cannot be visualized by any means during image-guided endovascular procedures. For aneurysm treatment with detachable coils, the thin strands of overlapping coils are typically blurred together into a dense mass with standard DA equipment. Visualization of the detailed shape of the aneurysm and the location and spacing of coil loops could foretell the outcome of the treatment. Finally, for AVM treatment with glue, present images are inadequate in allowing exact evaluation of the filling of small vessels to prevent recurrence.

SUMMARY OF THE INVENTION

Although there is a real need for substantially improved spatial resolution for the images used to guide endovascular procedures, this improvement is not necessarily needed throughout the course of the procedure for the full viewing field. Therefore, in accordance with the present invention it is proposed that improved images are needed only for a region of interest at the site of the intervention, and only during those times during the procedure when crucial decisions must be made either to modify or to end the procedure.

The present invention provides a radiographic imaging apparatus and method for vascular interventions for acquiring very high resolution radiographic images over a small region of interest (ROI). The apparatus and associated method employs digital solid state x-ray image detectors for the medical imaging application of angiography. A mechanical arrangement, for example an arm attached to an existing large area x-ray detector, allows the small area ROI digital detector to be temporarily positioned over a region located by the standard large area imager so that additional very high resolution digital images may be obtained over the ROI. Although large area spot film devices for analog screen/film combination detectors used in the past have better spatial resolution than the standard image intensifier (II) based systems generally used in medical angiographic facilities, the film must be chemically processed preventing an immediate display of the image and making not practicable the subtraction of background structures which is easily achievable with digital imagers. The present invention provides an entirely digital device of very high resolution for use in this small field of view spot imaging application which is capable of immediate image display as well as of mask image subtraction. The high resolution digital ROI imager can comprise an x-ray absorbent phosphor optically coupled to a fiber optic taper which minifies the image and presents it to one large area or an array of smaller charge coupled device (CCD) light sensors. The main application for the apparatus and method of the present invention appears to be during interventional procedures in the region of the intervention, generally near the catheter tip. In cerebrovascular interventions, smaller and smaller catheters, guide wires, and interventional devices such as stents and coils are being used which are difficult to visualize with conventional II-based imaging systems. The method and apparatus of the present invention thus provides a change in the design paradigm for radiographic detectors to optimize imaging of a region of interest for endovascular interventions.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1A is a schematic diagram illustrating the apparatus and method of the present invention;

FIG. 1B is a schematic diagram of the apparatus of the present invention illustrating an alternative for supporting and positioning the ROI detector;

DETAILED DESCRIPTION OF THE INVENTION

Figure 1C:
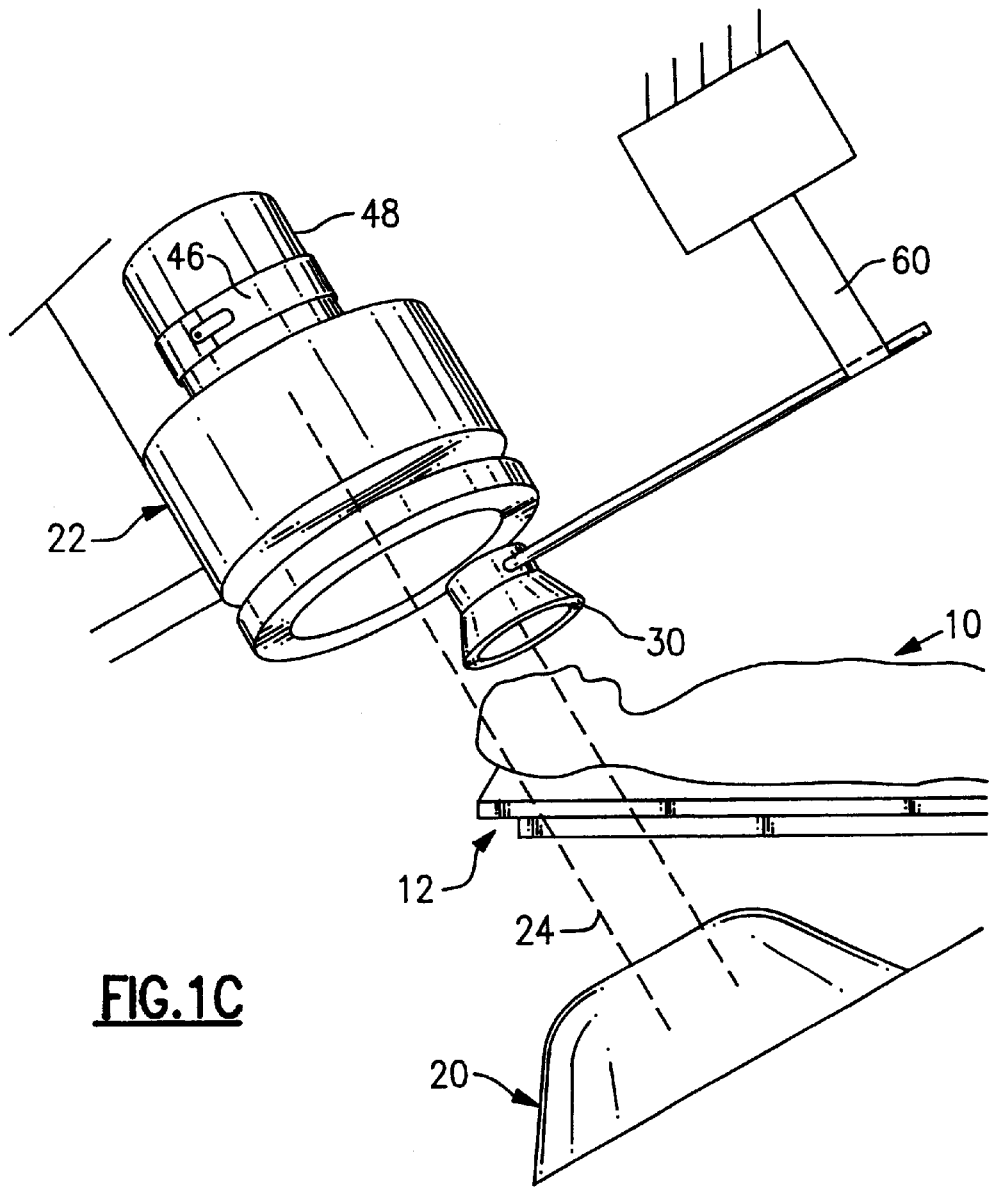
FIG. 1C is a schematic diagram of the apparatus of the present invention illustrating an alternative for supporting and positioning the ROI detector.

Differences in the rationale for imaging during endovascular interventions and during diagnostic angiography necessitate a paradigm change in the characterization of an optimal radiographic imaging system. Because endovascular interventions a) are usually done in small regions of interest (ROI) within a large field of view (FOV) where there is a priori known pathology, b) are temporally much longer procedures, and c) may involve devices and catheters of decreasing size, the past trade-offs related to geometry, dose, and spatial frequency response of the modulation transfer function (MTF) and the detective quantum efficiency (DQE) may no longer apply. By changing the design paradigm for radiographic imaging systems so as to require optimization in a ROI for endovascular interventions rather than for full FOV diagnostic systems, the present invention provides a new class of micro-angiographic detector.

In particular the present invention provides a radiographic imaging apparatus and method for vascular interventions for acquiring very high resolution radiographic images over a small region of interest (ROI). The apparatus and associated method employs digital solid state x-ray image detectors for the medical imaging application of angiography. The high resolution digital ROI imager can comprise an x-ray absorbent phosphor optically coupled to a fiber optic taper which presents the reduced image to charge coupled device (CCD) light sensors in a manner which will be described in further detail presently. A mechanical arrangement, for example an arm attached to an existing large area x-ray detector, allows the small area ROI digital detector to be temporarily positioned over a region located by the standard large area imager so that additional very high resolution digital images may be obtained over the ROI.

Referring to FIG. 1A, a patient 10 is resting on a table 12 or similar supporting surface and is located in proximity to standard radiographic apparatus comprising an x-ray tube 20 which is a source of x-rays and an image intensifier (II) or large area x-ray detector 22. In the situation illustrated in FIG. 1A, the central ray or central axis 24 extending between x-ray tube 20 and image intensifier 22 passes through the head of patient 10 for obtaining radiographic images at related locations in the patients head. Other areas of the patients' body can of course be imaged by the apparatus shown in FIG. 1A, including the apparatus of the present invention.

The region of interest (ROI) detector 30 according to the present invention is shown in FIG. 1A moved into a position where it is in alignment or in operative position with respect to central ray 24. In addition, the image plane of detector 30 is substantially parallel to and in close proximity to the image plane of image intensifier 22. This is the operative position where detector 30 is used to enable the operating physician to monitor an endovascular interventional procedure, such as in the head area of patient 10 in the situation illustrated in FIG. 1A. Detector 30 would be operatively connected to equipment including a CRT video monitor or display (not shown) providing visual images of the procedure as it is taking place. Such monitors or displays and associated equipment are well-known to those skilled in the art so that a detailed description thereof is believed to be unnecessary. Detector 30 also can be operatively connected to equipment for taking successive film records of the images in a manner known to those skilled in the art.

Detector 30 is carried by the image intensifier 22 in manner so that it can be moved to the broken line position shown in FIG. 1A where it is away from central ray or axis 24 when it is not in use. By way of example, in an illustrative situation, at the beginning of an interventional procedure, i.e. during the initial installation of a stent, the procedure typically will be monitored using the standard image intensifier 22 in which case ROI detector 30 is moved to the broken line position in FIG. 1A where it is out of alignment with central ray 24. During the procedure where improved images are needed at the site of the intervention and where crucial decisions must be made such as modifying or ending the procedure, ROI detector 30 is moved to the solid line position of FIG. 1A where it is in alignment with central ray 24 whereupon detector 30 provides the images viewed by the operating physician. Thereafter, detector 30 is returned to the broken line position shown in FIG. 1A.

In the illustrative arrangement of FIG. 1A, detector 30 is fixed to one end of an arm 40, the opposite end of which is pivotally connected by a mechanism 42 to one end of a second arm 44, the opposite end of which is fixed by a collar or suitable mounting bracket 46 to the smaller diameter neck position 48 of image intensifier 22. Thus, arm 42 which carries detector 30 is pivoted about an axis substantially parallel to central ray axis 24. Arm 44 can of course be mounted to other locations on the body or housing of image intensifier 22.

The arrangement of FIG. 1A is illustrative of various other ways ROI detector 30 can be supported and positioned according to the present invention. For example, as shown in FIG. 1B one alternative can include a pair of spaced parallel rails 50 disposed substantially perpendicular to central ray axis 24 and carried by brackets 52 fixed to image intensifier 22. Detector 30 would be movable along the rails, typically by roller bearings 54 or the like, into and out of alignment with central ray 24. This arrangement therefore is characterized by translatory movement of detector 30 in contrast to the pivotal or swinging movement of detector 30 in FIG. 1A.

While both of the foregoing arrangements preferably feature the detector 30 movably carried by or on the image intensifier 22, as shown in FIG. 1C it is within the scope of the present invention to have detector 30 carried by a frame 60 or supporting structure separate from image intensifier 22 and provided with an arrangement for swinging or translatory movement of detector 30, or detector 30 could be carried by a moveable frame, cart or equivalent structure which itself is moved to position detector 30 in alignment with central ray axis 24.

Figure 1D:
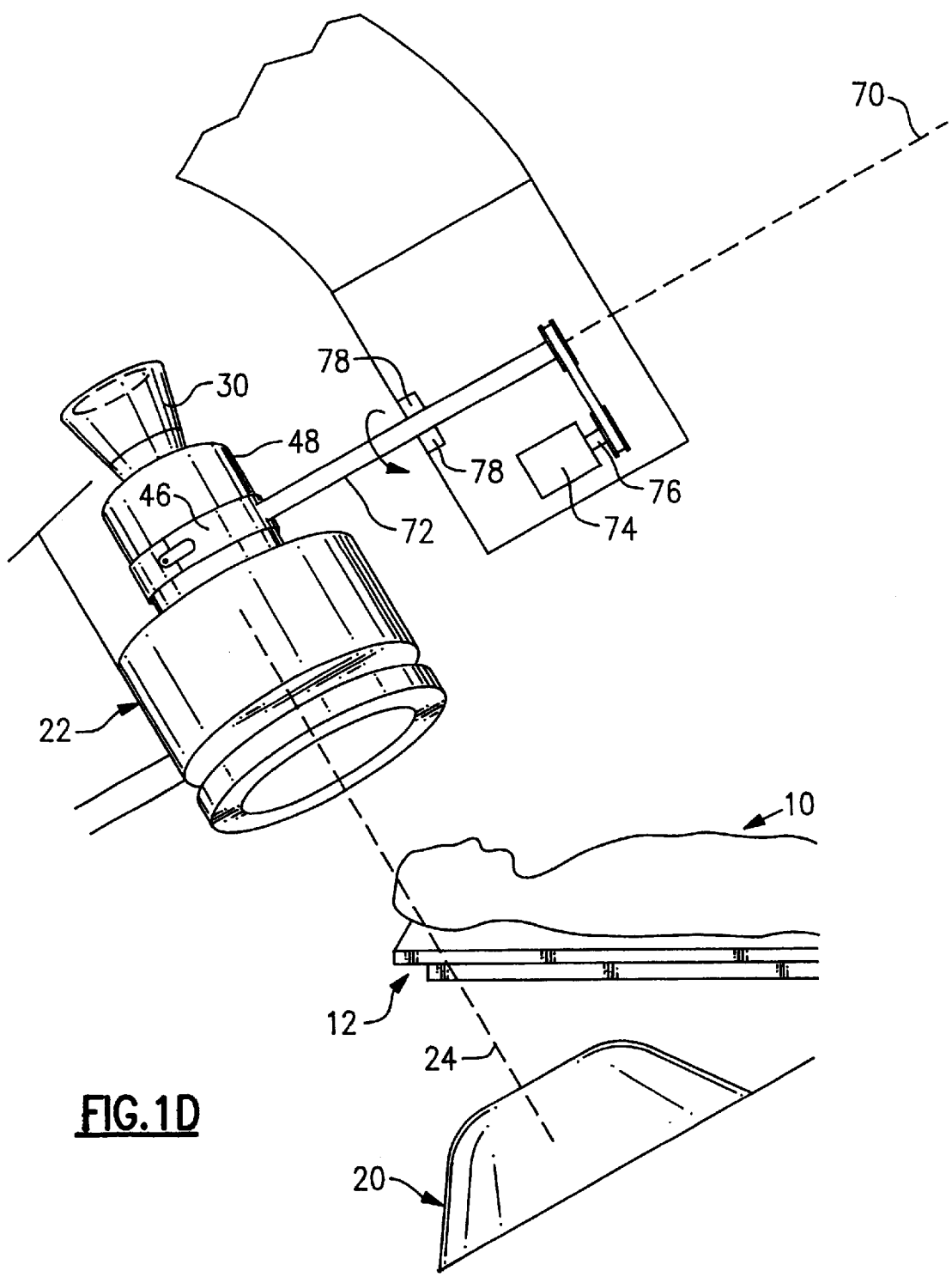
FIG. 1D is a schematic diagram of the apparatus of the present invention illustrating an alternative for supporting and positioning the ROI detector.

Another alternative arrangement shown in FIG. 1D includes ROI detector 30 fixed to image intensifier (II) 22 with the combination of detector 30 and II 22 mounted for rotation about an axis 70 perpendicular to central ray axis 24. As known to those of skill in the art, the rotation can be accomplished by a rotating shaft 72 coupled to an electric motor 74 through a speed reducer 76. The shaft 72 is preferably supported by bearings 78. The arrangement could dispose the image planes of II 22 and detector 30 at right angles to each other, and the combination then would be rotated 90° about the afore-mentioned axis to selectively place either II 22 in alignment with central ray axis 24 or detector 30 in alignment with axis 24 as needed depending upon the particular stage of the interventional procedure being carried out. Alternatively, the arrangement could dispose the image planes of II 22 and detector 30 at 180° to each other, i.e. facing at opposite ends of the arrangement, and the combination then would be rotated selectively about the afore-mentioned axis to selectively place either II 22 or detector 30 in alignment with central ray axis 24.

Figure 1E:
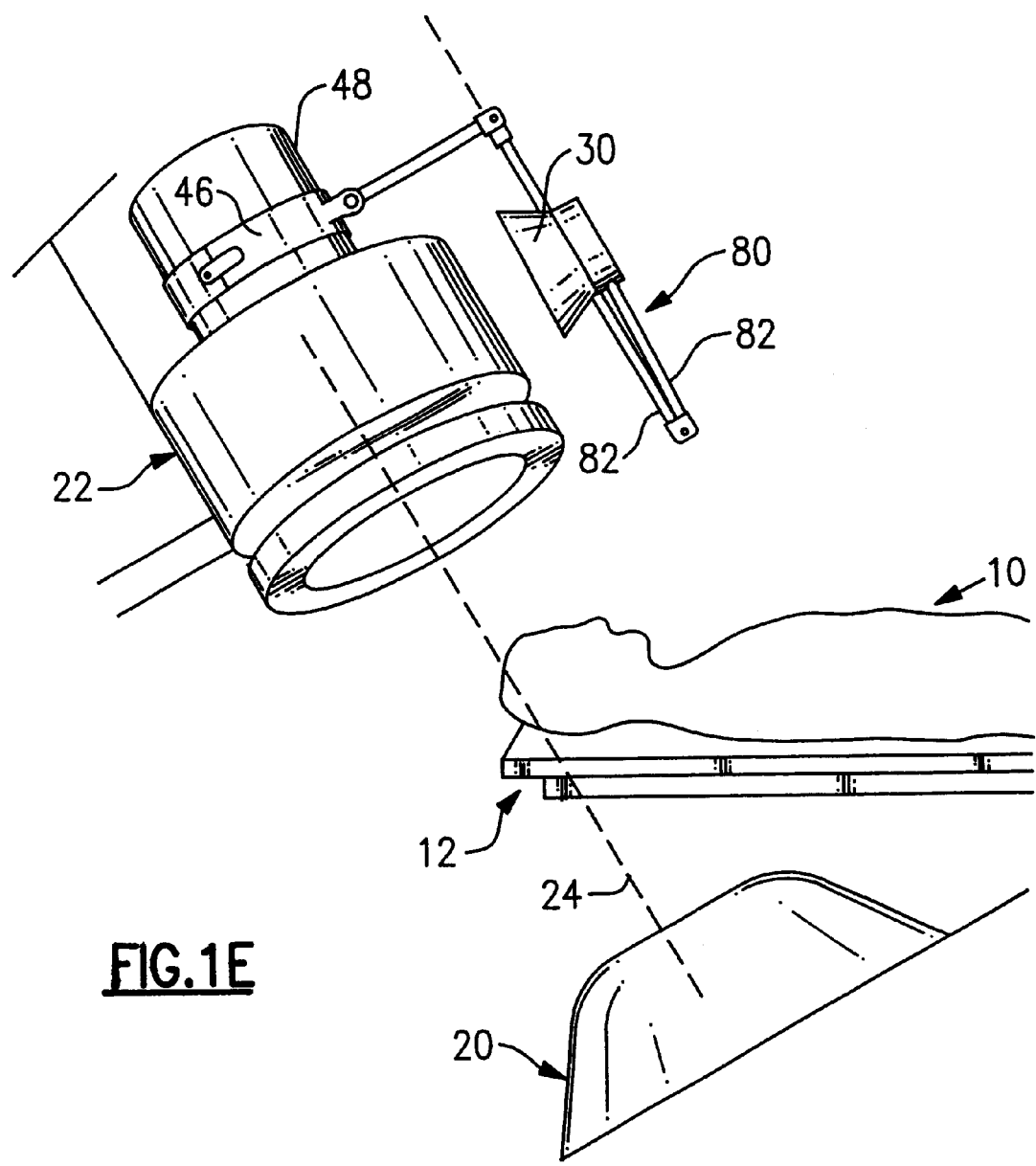
FIG. 1E is a schematic diagram of the apparatus of the present invention illustrating an alternative for supporting and positioning the ROI detector.

As shown in FIG. 1E, still another alternative arrangement could include an articulated arm structure 80 with detector 30 carried on one end of the arm structure 80 and with the other end of the arm structure 80 mounted on the housing of image intensifier 22 in a suitable manner. The articulated arm 80 comprises pivotally and rotatably connected members 82 capable of pivoting and rotating into and away from the field of view. The articulation of the arm structure 82 would enable it to place detector 30 in the solid line position shown in FIG. 1A when it is in use whereupon the arm structure and detector 30 could be moved or folded to a "parked" position, shown in FIG. 1E, out of alignment with central ray 24 and located so as not to interfere with operation or use of II 22 or any other equipment and so as not to interfere with medical personnel performing the intervention procedure. Articulated arm structures having pivotally connected members are well known to those of ordinary skill in the art. Detailed examples of articulated arm structures are found in U.S. Pat. No. 5,820,623 entitled "Articulated Arm for Medical Procedures" and U.S. Pat. No. 4,492,119 entitled "Articulated Arm Ultrasound Imaging Systems", both of which are incorporated by reference.

The foregoing description is not meant to be exhaustive but merely illustrative of the numerous ways ROI detector 30 can be supported and positioned within the scope of the present invention.

Figure 2:
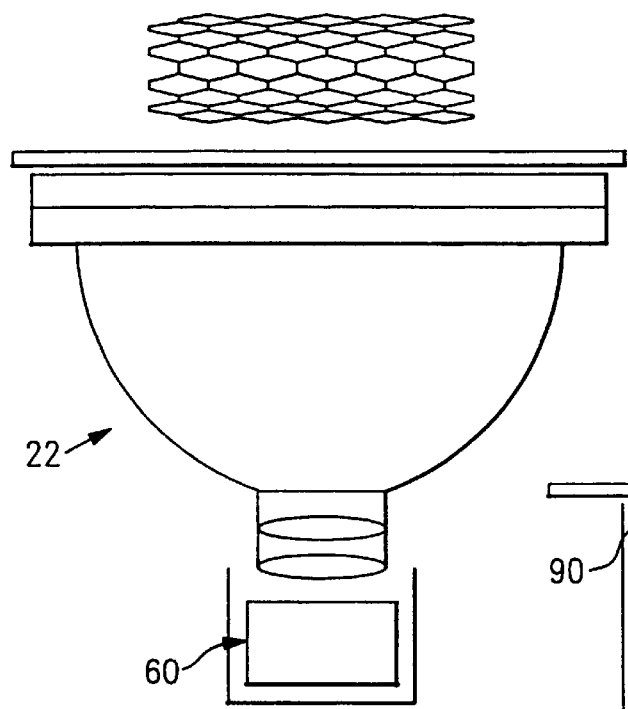
FIG. 2 is a schematic diagram of the standard image intensifier in the arrangement of FIG. 1A.

FIG. 2 illustrates in further detail an example of image intensifier 22 in the form of a standard digital subtraction angiography (DSA) image intensifier (II) detector. A standard DSA unit is commercially available from Toshiba under Model No. TDA4000 with a 12 inch image intensifier (approximately 200 mg/cm$^2$ CsI) used in its highest (4.5 inch) magnification mode. There is an optionally coupled CCD video camera 60 with 1024×1024 matrix size for a pixel size of 110 µm and a 10-bit grayscale.

Figure 3:
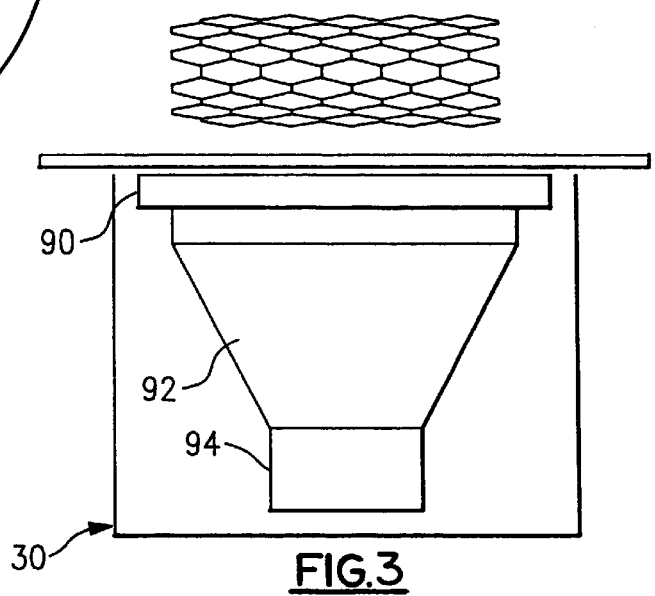
FIG. 3 is a schematic diagram of the region of interest detector in the arrangement of FIG. 1A.

FIG. 3 illustrates in further detail one form of ROI detector 30 which includes an x-ray absorbent phosphor 90 optically coupled to a fiber optic taper 92 which presents a reduced image to a charge coupled device (CCD) camera 94. Other forms of high resolution radiographic detectors may also be used for a high resolution region of interest x-ray detector. Of the various designs for a high resolution ROI radiographic detector, the CCD based indirect detector appears to be most practical at the present time. In theory, the direct detector such as those with amorphous Se can have better resolution (superior pre-sampled modulation transfer function at high frequencies); however, such flat panel devices in static imaging mode have been limited to larger pixel sizes due to fill factor limitations. For more rapid angiographic application, pixel sizes in excess of 150 µm have been reported.

While a flat panel device would be preferred due to space constraints, there are also problems with indirect detectors which use a phosphor screen with a light detector. Of indirect detectors, the pixel size is too large for similar reasons as for the direct flat panel devices. In addition to the thin film transistor (TFT) fill factor restrictions, there are spatial restrictions to reducing the size of the photo-diode, storage capacitor combination needed for the indirect flat panel detectors. The smallest cell size for commercially available indirect detectors is 127 µm although proprietary designs for direct detectors down to 80 µm have been reported.

Accordingly, a CCD-fiberoptic taper combination design is disclosed for x-ray detector 30. However, as discussed above a high resolution direct flat panel detector such as a selenium plate overlayed with a thin film transistor could also be used if the pixel size could be reduced to about 50 µm. Also, as discussed above an indirect flat panel detector with a photodiode array directly viewing an x-ray sensitive phosphor, such that the charge stored near each photodiode in the array can be read out using a TFT array, may be used as an ROI x-ray detector. Finally, although the preferred embodiments of the invention disclose a fiberoptic taper, the need for a taper may be eliminated if the CCD chip is large enough such that the x-ray converter phosphor can be directly deposited on the CCD.

By way of example, detector 30 can comprise a micro-angiographic detector including a Model H7345 Type E Hamamatsu CCD camera with standard RS-170 interlaced video signal and with a 3:1 tapered fiber-optic reducer. The CCD output is digitized providing a matrix size of 480×512 with 8-bit grayscale. The effective area in the phosphor plane is 11.1×14.7 mm$^2$ with a 23 µm effective pixel size. The phosphor module is a Hamamatsu Model J6671 with 40 mg/cm$^2$ of CsI(TI) resulting in 11–12 lp/mm spatial revolution measured using a Nuclear Associates Model 07-555 bar pattern.

Figure 6:
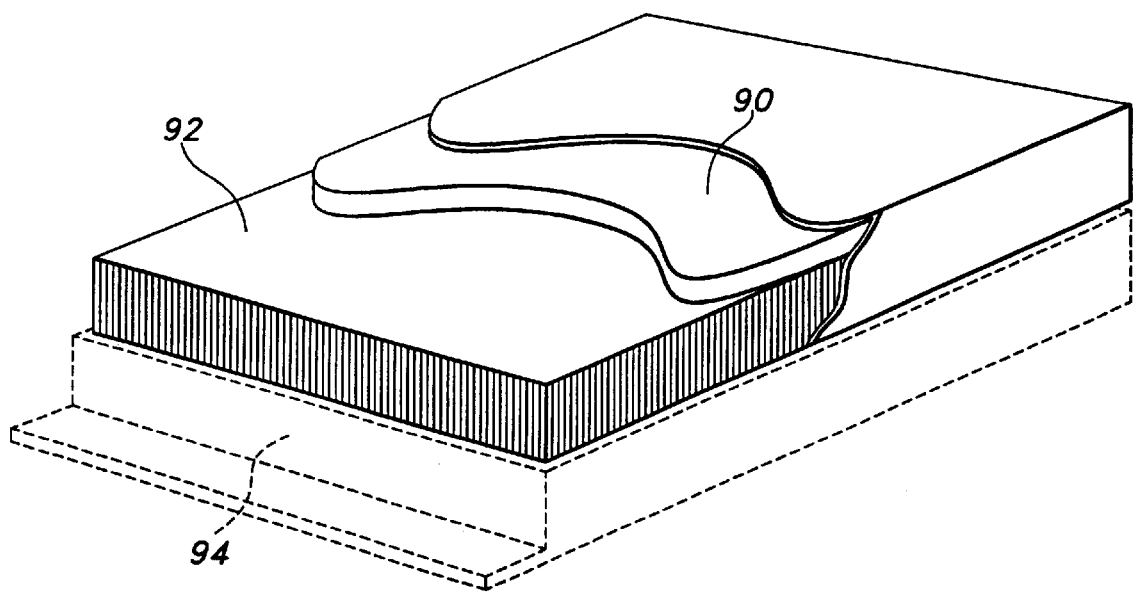
FIG. 6 is a perspective cutaway view of the layers of a phosphor module.

As shown in FIG. 6, a singular layer of the converter material is applied to the fiber optic plate, and accordingly, the converter material for this module is undivided.

The present invention is illustrated further by the following examples.

EXAMPLE I

A ROI interventional radiographic imager, like detector 30 of FIG. 1A, optimized for high spatial resolution over a fraction of conventional FOV was investigated which accepts compromises in x-ray absorption or low frequency DQE (hence increased dose per frame) so that the high frequency DQE required to visualize very fine stent wires and vessels as well as details of stenoses and aneurysm could be achieved. A prototype system based upon a 40 mg/cm$^2$ CsI(TI) x-ray converter optically coupled to a CCD array using a fiber taper was compared with a state-of-the-art-image-intensifier-based digital angiographic (DA) system, an extremity film/screen cassette, and a non-screen/film detector. The systems were compared for imaging typical neuro-vascular pathologies (stenoses, aneurysms, arterio-venous malformations (AVMs)) and a variety of stents with wire diameter down to 50 µm. Geometric unsharpness was minimized.

The cut-off frequency of the non-screen film was highest (over 20 lp/mm); that of the DA system was lowest (3–4 lp/mm), while that of the prototype CCD/fiber taper detector (11–12 lp/mm) was slightly higher than that of the extremity cassette. Although the zero frequency DQE of the DA unit and screen/film system exceeded that of the prototype with its thin phosphor layer, the prototype excelled in the desired frequency range of 3–10 lp/mm. To demonstrate this further a Nuclear Associates Model 76-705 artery block phantom which has 1, 2, and 3 mm diameter stenoses and aneurysms was radiographed. The smallest stenoses and aneurysm were clearly visualized only with the prototype. For imaging stents, it was demonstrated clearly that details of wires and struts were visible only with the prototype. Finally, prototype images of an AVM model using a pig rete showed qualitatively more detailed angio-architecture compared to blurred-appearing standard DA images.

By providing digital imaging capability in the 3–10 lp/mm spatial frequency range for small field of view angiographic images used to guide endovascular interventional procedures, details of device deployment (aneurysm coil spacing, stent wire and weld condition), and visualization of crucial 50–300 $\mu$m brain perforator vessels will become available during the course of neuro-interventions for the first time. It is expected that this new capability should allow improved treatments and further development of smaller interventional devices and catheter delivery systems.

EXAMPLE II

A high spatial resolution region of interest (ROI) micro-angiographic x-ray camera like that shown in FIG. 3 was compared with a standard digital subtraction angiographic (DSA) unit like that shown in FIG. 2 for delineating vascular stent status such as condition of struts, wires, and welds.

Figure 4:
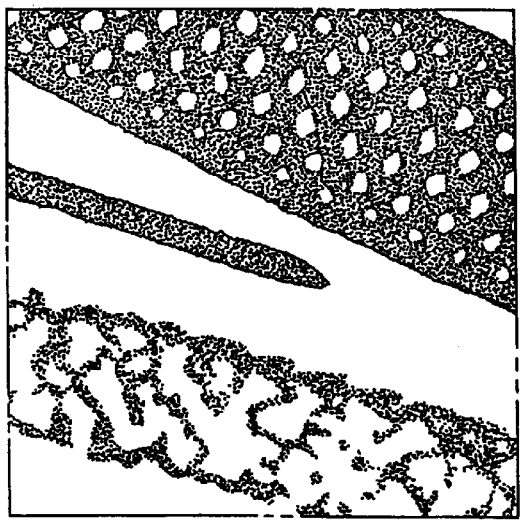
FIGS. 4 and 5 are images obtained by Standard DSA equipment and by the detector of the present invention, respectively.
Figure 5:
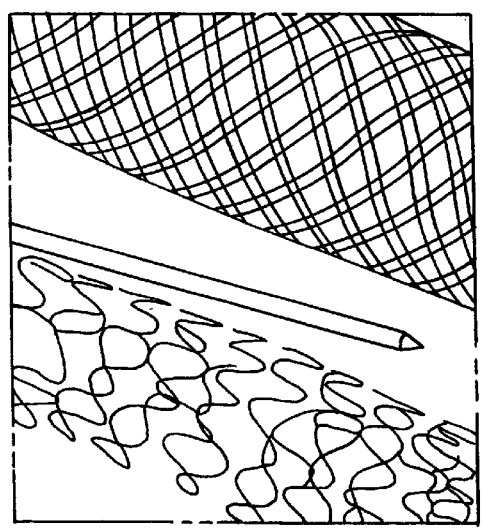

Eleven stents of varying design, both balloon expandable and self expanding, with wire or strut size ranging from $50\mu$ to $225\mu$ made of either nitinol or stainless steel were imaged both with standard DSA equipment (Toshiba CAS-8000V, $1024^2$, 10 bit, $110\mu$ pixels) using the highest (4.5 inch) magnification mode and with a prototype CCD/fiber-optic taper ROI detector with 40 mg/cm$^2$ of CsI(Tl) phosphor x-ray to light converter. The new camera exhibited better than eleven lp/mm resolution using a standard gold bar pattern and had $23\mu$ pixel size compared to $110\mu$ for the DSA unit. No scattering media, negligible geometric unsharpness, and exposures at 70 kVp isolated the test to a comparison of the detectors. An example of the foregoing is provided by the image of FIG. 4 obtained by the standard DSA equipment and the image of FIG. 5 obtained by the detector of the present invention.

Although absorption efficiency of the prototype's thin phosphor layer is about one third that for standard image intensifiers, spatial resolution is substantially better. Details of stent condition such as wire bends, defects, and connecting struts and welds were better visualized with the prototype. For the smallest stent with $50\mu$ wire, only the prototype device could visualize the complete pattern of the mesh while for the DSA unit, sections of the wire were obliterated on the images. For another stent, the bends where $80\mu$ steel wires crossed to form the stent mesh were clearly depicted with the prototype camera but not seen at all with the standard DSA unit.

As an alternative, a high resolution ROI camera having a much larger field of view may be used for detector 30. The larger detector also has a CsI(Tl)phosphor deposited upon a fiberoptic plate that is optically coupled to a fiberoptic taper which in turn is coupled to the CCD. The field of view is 5 cm×5 cm compared to the previous 1 cm×1 cm. Although the phosphor material is the same, the absorption efficiency is increased by using a 350–400 $\mu$m thick layer (Model J6677HL, Hamamatsu Corp., Bridgewater, N.J.). Although the MTF is slightly compromised, the objective of viewing at least 10 line pairs/millimeter (lp/mm) is maintained. The CCD used in the camera (Model THX7899MCRH, Thomson-CSF, Totowa, N.J.) is larger (2048 pixels each of 14 micron dimension) and therefore the fiberoptic taper minification ratio is reduced to 1.8 from the 3.0 ratio of the smaller camera. The change in ratio resulted in a 2.8× improvement in light collection. In order to keep the number of pixels per image manageable all images had pixels binned 2:1 so that the effective pixel size at the phosphor was 50 microns for a 1024×1024 matrix size.

The camera, camera control, and computer interface is Model TH2048-CFX (MedOptics Corp., Tucson, Ariz.) and is provided with software allowing offset, gain and dark current correction. The dark current is typically negligible because of the thermoelectric cooler and amounts to less than a few analog to digital units (ADU). The offset is typically 180 ADU and is reproducible and easily subtracted from all images after a zero exposure image was recorded. The gain or flat field correction is required to eliminate the typical superimposed hexagonal background structure caused by the fiberoptic elements. Typically, at least 32 frames are averaged to reduce the contribution of quantum noise from this flat field correction to negligible levels. The maximum signal output of the system for each pixel is approximately 16,000 which is consistent with the 14 bit digitalization used. The rated readout noise of less than 25 electrons per pixel is equivalent to less than a few ADU.

Because the CCD is of the full frame rather than the interline or frame transfer design, it is necessary to take some care in synchronizing the image record cycle of the camera with the pulsed x-ray exposure. For proper operation, the continuing row dumping cycle used to reduce dark current accumulation must be suspended just prior to x-ray exposure which must be followed by sequential readout and digitization. Also, any frame clear cycle must be concluded. Initially, when purely manual exposure control was used, there was the requirement for a short delay before initiating x-ray exposure while the camera changed from the charge dumping or clear conditions to the accumulation condition. If the x-ray exposure should occur during a frame clear, cut-off, displacement, and blurring of the image can result. An independent trigger pulse derived from a separate x-ray sensor can also be used to address the synchronization issue.

As smaller or finer stents are used to treat vascular pathologies more precisely, higher spatial resolution will be required; however, this improvement may be needed only over a small ROI around the stent deployment site. The new ROI micro-angiographic detector has sufficiently high spatial resolution over a limited field of view to visualize many important features of stents which current DSA imaging equipment cannot.

Referring again to FIG. 1C, x-ray tube 20 includes a source of x-rays and a collimator as is well known by those skilled in the art. It is within the scope of the present invention to move ROI detector 30 a short distance out of alignment with central ray 24 in response to a request from the operating physician for viewing a desired location, and in response to such movement of detector 30 it is also within the scope of the present invention to move the location of the x-ray beam by moving the collimator to follow the field of view of ROI detector 30. In particular, this would be accomplished by moving the appropriate parts of the collimator to allow the x-ray beam to maintain registration with the location of ROI detector 30 so that the beam always is collimated to the sensitive area of ROI detector 30.

As an alternative to detector 30 shown in FIG. 3, a small flat panel detector could be employed provided the pixel size were smaller than those presently available. In this regard, selenium-based photo-conductors appear to be of interest provided the pixel size can be reduced. A further alternative could be a flat panel detector of large area made so that each pixel is very small and of very high resolution. While it would be impractical to take the whole image out, it would be possible to bin the pixels in the bulk of the area, i.e., put the pixels together, so that only a certain ROI would be of high resolution. That ROI of the detector could be moved around electronically to accomplish this region of interest imaging.

In conclusion, by changing the design paradigm for radiographic detectors to optimize imaging of a region of interest (ROI) for endovascular interventions, a new class of micro-angiographic detectors is provided. Such ROI imagers optimized for high spatial resolution over a fraction of the conventional FOV accept compromises in x-ray absorption so that the desired high frequency DQE is achieved. A prototype demonstration system based upon a CsI(Tl) phosphor coupled by a fiber taper to a CCD as shown in FIG. 3 was compared with an image-intensifier-based digital angiographic (DA) system as shown in FIG. 2 for imaging typical neuro-vascular pathologies (stenoses, aneurysms, arterio-venous malformations (AVMs)) and a variety of stents with wire diameter down to 50 $\mu$m. Although the zero frequency DQE of the DA unit exceeded that of the prototype with its thin phosphor layer, the prototype excelled in the desired frequency range of 3–10 lp/mm. Using an artery block phantom, the smallest 1 mm diameter stenoses and aneurysms were clearly visualized only with the prototype. For imaging stents, details of wires and struts were only visible with the prototype. ROI images of an AVM pig rete model showed more detailed angio-architecture compared to blurred-appearing DA images. It is expected that such ROI cameras shown allow improved clinical interventions. By providing digital imaging capability in the 3–10 lp/mm spatial frequency range for small field of view angiographic images used to guide endovascular interventional procedures, details of device deployment (aneurysm coil spacing, stent wire and weld condition), and visualization of crucial 50–300 $\mu$m brain perforator vessels will become available during the course of neuro-interventions for the first time. It is expected that this new capability should allow improved treatments and further development of smaller interventional devices and catheter delivery system. The potential applications include image guided catheter-based interventional procedures where the region of interest is near the interventional site, usually at the catheter tip. The accuracy of procedures such as stent deployments, placement of embolic material or devices, and precise localization of pathologic features such as aneurysm necks, stenotic magnitude and asymmetries, and micro-angio-architecture of arteriovenous malformations may be improved using the proposed method. The method is compatible with existing commercial fluoroscopic and angiographic equipment.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A radiographic imaging apparatus, comprising:
   an x-ray source irradiating an object to be inspected with x-rays;
   a fluoroscopic x-ray image detector capable of receiving the x-rays which pass through the object and converting the received x-rays into a first output;
   a display capable of picking up the first output; and,
   an x-ray detector element having an undivided converter material capable of receiving the x-rays which pass through the object to produce signals corresponding to the x-rays, the x-ray detector element converting the signals into a second digital output;
   wherein the x-ray detector element is capable of providing higher spatial resolution images of a region of interest detected by the fluoroscopic x-ray image detector.

2. The radiographic imaging apparatus of claim 1, wherein the fluoroscopic x-ray image detector comprises an image intensifier tube.

3. The radiographic imaging apparatus of claim 1, wherein the fluoroscopic x-ray image detector comprises a direct conversion flat panel device.

4. The radiographic imaging apparatus of claim 1, wherein the fluoroscopic x-ray image detector comprises an indirect conversion flat panel device.

5. The radiographic imaging apparatus of claim 1, wherein the x-ray detector element is a direct conversion flat panel device.

6. The radiographic imaging apparatus of claim 1, wherein the x-ray detector element is an indirect conversion flat panel device.

7. The radiographic imaging apparatus of claim 1, wherein the x-ray detector element is a scintillator screen optically coupled to a CCD camera.

8. The radiographic imaging apparatus of claim 7, wherein the scintillator screen comprises phosphor.

9. The radiographic imaging apparatus of claim 7, further comprising a focusing element disposed between the scintillator screen and the CCD camera.

10. The radiographic imaging apparatus of claim 9, wherein the focusing element is a fiberoptic reducer.

11. The radiographic imaging apparatus of claim 9, wherein the focusing element is a lens.

12. A radiographic imaging apparatus, comprising:
    an x-ray source irradiating an object to be inspected with x-rays;
    a fluoroscopic x-ray image detector capable of receiving the x-rays which pass through the object and converting the received x-rays into a first output;
    a display capable of picking up the first output; and,
    an x-ray detector element capable of receiving the x-rays which pass through the object and converting the x-ray radiation into a second digital output;
    wherein the spatial resolution of the x-ray detector element is approximately 3 to 10 lp/mm and the x-ray detector element is capable of providing higher spatial resolution images of a region of interest detected by the fluoroscopic x-ray image detector.

13. A radiographic imaging apparatus, comprising:
    a frame;
    an x-ray source mounted on the frame and capable of irradiating an object placed in the apparatus;
    a fluoroscopic x-ray image detector capable of receiving the x-rays which pass through the object and converting the received x-rays into a first output;
    a display capable of picking up the first output; and,
    an x-ray detector element capable of receiving the x-rays which pass through the object and converting the x-ray radiation into a second digital output, the x-ray detector element retractably mounted to the frame such that it is capable of receiving the x-rays in a deployed position and such that it does not interfere with the fluoroscopic x-ray image detector in a stored position;

wherein the x-ray detector element is capable of providing higher spatial resolution images of a region of interest detected by the fluoroscopic x-ray image detector.

14. The radiographic imaging apparatus of claim 13, wherein the fluoroscopic x-ray image detector comprises an image intensifier tube.

15. The radiographic imaging apparatus of claim 13, wherein the fluoroscopic x-ray image detector comprises a direct conversion flat panel device.

16. The radiographic imaging apparatus of claim 13, wherein the fluoroscopic x-ray image detector comprises an indirect conversion flat panel device.

17. The radiographic imaging apparatus of claim 13, wherein the x-ray detector element is a direct conversion flat panel device.

18. The radiographic imaging apparatus of claim 13, wherein the x-ray detector element is an indirect conversion flat panel device.

19. The radiographic imaging apparatus of claim 13, wherein the x-ray detector element is a scintillator screen optically coupled to a CCD camera.

20. The radiographic imaging apparatus of claim 19, wherein the scintillator screen comprises phosphor.

21. The radiographic imaging apparatus of claim 19, further comprising a focusing element disposed between the scintillator screen and the CCD camera.

22. The radiographic imaging apparatus of claim 21, wherein the focusing element is a fiber optic reducer.

23. The radiographic imaging apparatus of claim 21, wherein the focusing element is a lens.

24. The radiographic imaging apparatus of claim 13, wherein the spatial resolution of the x-ray image detector is approximately 3 to 10 lp/mm.

25. The radiographic imaging apparatus of claim 13, wherein the x-ray detector element is mounted on an arm that is rotatably attached to the frame.

26. The radiographic imaging apparatus of claim 13, wherein the x-ray detector element is mounted on an articulating arm that is attached to the frame.

27. The radiographic imaging apparatus of claim 13, wherein the x-ray detector element is slidably mounted on a rail that is attached to the frame.

28. The radiographic imaging apparatus of claim 13, wherein the x-ray detector element is mounted on a support structure that is independent from the frame.

29. The radiographic imaging apparatus of claim 13, wherein the x-ray detector element and the fluoroscopic x-ray image detector are mounted on a rotating turret attached to the frame such that the image detector and the x-ray detector element are capable of being rotated respectively into a position to receive the x-ray radiation from the x-ray source.

30. A radiographic imaging method, comprising the steps of:
providing an x-ray source capable of irradiating an object;
providing a fluoroscopic x-ray image detector capable of receiving the x-rays that pass through the object and converting the x-rays into a first output;
placing an object between the x-ray source and the x-ray image detector;
performing a procedure on the object with aid of radiographic imaging guidance from the fluoroscopic x-ray image detector;
determining a region of interest within a field of view of the fluoroscopic x-ray image detector;
providing an x-ray detector element having an undivided converter material capable of receiving the x-rays that pass through the object in the region of interest to produce signals corresponding to the x-rays, the x-ray detector element capable of converting the signals into a second digital output, the x-ray detector element having a higher spatial resolution than the x-ray image detector; and,
viewing an image picked up from the second output.

31. The method of claim 30, wherein the fluoroscopic x-ray image detector is an x-ray image intensifier tube.

32. The method of claim 30, wherein the fluoroscopic x-ray image detector is a direct conversion flat panel detector.

33. The method of claim 30, wherein the fluoroscopic x-ray image detector is an indirect conversion flat panel detector.

34. The method of claim 30, wherein the x-ray detector element is a direct conversion flat panel device.

35. The method of claim 30, wherein the x-ray detector element is an indirect conversion flat panel device.

36. The method of claim 30, wherein the x-ray detector element is a scintillator screen optically coupled to a CCD camera.

37. The method of claim 36, wherein the scintillator screen comprises phosphor.

38. A method for radiographic imaging, comprising the steps of;
providing a flat panel x-ray image detector having an array of pixels with a size of 25–50 $\mu$m;
electronically dividing the flat panel x-ray image detector into zones to establish a high resolution mode for region of interest viewing;
binning the pixels to provide a large area mode for the x-ray image detector having an effective pixel size of at least 100 $\mu$m; and
viewing an irradiated object in the large area mode of x-ray detection to detect a region of interest;
switching the x-ray image detector to the high resolution mode in one of the zones; and,
viewing the object in the region of interest in the high resolution mode.

39. The method of claim 38, further comprising the step of providing a display capable of displaying the large area field of view and the region of interest field of view simultaneously.

40. A radiographic imaging method, comprising the steps of:
providing an x-ray source mounted on a frame and capable of irradiating an object;
providing a fluoroscopic x-ray image detector capable of receiving the x-rays that pass through the object and converting the x-rays into a first output;
placing an object between the x-ray source and the x-ray image detector;
performing a procedure on the object with aid of radiographic imaging guidance from the fluoroscopic x-ray image detector;
determining a region of interest within a field of view of the fluoroscopic x-ray image detector;
providing an x-ray detector element capable of receiving the x-rays that pass through the object in the region of interest and capable of converting the x-rays into a second digital output, the x-ray detector element having a higher spatial resolution than the x-ray image detector, the x-ray detector element retractably mounted to the frame such that it is capable of receiving the x-rays in a deployed position and such that it does not interfere with the fluoroscopic x-ray image detector in a stored position; and, viewing an image picked up from the second output.

41. The method of claim 40, wherein the fluoroscopic x-ray image detector is an x-ray image intensifier tube.

42. The method of claim 40, wherein the fluoroscopic x-ray image detector is a direct conversion flat panel detector.

43. The method of claim 40, wherein the fluoroscopic x-ray image detector is an indirect conversion flat panel detector.

44. The method of claim 40, wherein the x-ray detector element is a direct conversion flat panel device.

45. The method of claim 40, wherein the x-ray detector element is an indirect conversion flat panel device.

46. The method of claim 40, wherein the x-ray detector element is a scintillator screen optically coupled to a CCD camera.

47. The method of claim 46, wherein the scintillator screen comprises phosphor.

* * * * *